(12) United States Patent
Kobayashi et al.

(10) Patent No.: US 7,732,638 B2
(45) Date of Patent: Jun. 8, 2010

(54) METHOD OF AMIDOCARBONYLATION REACTION

(75) Inventors: Shu Kobayashi, Tokyo (JP); Ryo Akiyama, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 758 days.

(21) Appl. No.: 10/592,138

(22) PCT Filed: Mar. 10, 2005

(86) PCT No.: PCT/JP2005/004715

§ 371 (c)(1),
(2), (4) Date: Nov. 8, 2006

(87) PCT Pub. No.: WO2005/085180

PCT Pub. Date: Sep. 15, 2005

(65) Prior Publication Data

US 2007/0197765 A1 Aug. 23, 2007

(30) Foreign Application Priority Data

Mar. 10, 2004 (JP) .............................. 2004-068206

(51) Int. Cl.
C07C 231/12 (2006.01)
C07C 231/10 (2006.01)
C07C 233/47 (2006.01)
C07C 233/82 (2006.01)
C07C 275/18 (2006.01)
C07B 61/00 (2006.01)
C08L 25/02 (2006.01)
C08L 29/10 (2006.01)

(52) U.S. Cl. ....................................... 562/575; 562/553
(58) Field of Classification Search .................. 562/553
See application file for complete search history.

(56) References Cited

U.S. PATENT DOCUMENTS 6,838,585 B2 * 1/2005 Spivak ......................... 585/25

OTHER PUBLICATIONS

Akiyama et al., 689 J. Organomet. Chem., 3806-3809 (2004).*
F.A. Dörwald, Side Reactions in Organic Synthesis, IX and 1-15 (2005).*
Niu et al., 123 J. Am. Chem. Soc., 6840 (2001.*
Okamoto et al., 127 J. Amer. Chem. Soc., 2125 (2005).*
H. Wakamatsu et al., "Synthesis of N-Acyl Amino-acids by a Carbonylation Reaction", J. Chem. Soc., Chem. Commun. 1540, 1971.

Matthias Beller et al., "Palladium-Catalyzed Amidocarbonylation—A New, Efficient Synthesis of N-Acyl Amino Acids", Angew. Chem., Int. Ed., 36, pp. 1494-1496, 1997.
Takahiro Sagae et al., "Platinum-catalyzed Amidocarbonylation", Chemistry Letters, vol. 32, No. 2, pp. 160-161, 2003.
Shü Kobayashi et al., "A Microencapsulated Lewis Acid. A New Type of Polymer-Supported Lewis Acid Catalyst of Wide Utility in Organic Synthesis", J. Am. Chem. Soc., 120, pp. 2985-2986, 1998.
Satoshi Nagayama et al., "Microencapsulated Osmium Tetraoxide. A New Recoverable and Reusable Polymer-Supported Osmium Catalyst for Dihydroxylation of Olefins", J. Org. Chem., 63, pp. 6094-6095, 1998.
Shü Kobayashi et al., "Catalytic Asymmetric Dihydroxylation of Olefins Using a Recoverable and Reusable Polymer-Supported Osmium Catalyst", J. Am. Chem. Soc., 121, pp. 11229-11230, 1999.
Shü Kobayashi et al., Catalytic Asymmetric Dihydroxylation Using Phenoxyethomethyl-polystyrene (PEM)-Based Novel Microencapsulated Osmium Tetroxide (PEM-MC $OsO_4$), Organic Letters, vol. 3, No. 17, pp. 2649-2652, 2001.
Ryo Akiyama et al., "Microencapsulated Palladium Catalysts: Allylic Substitution and Suzuki Coupling Using a Recoverable and Reusable Polymer-Supported Palladium Catalyst", Angew. Chem., Int. Ed., 40, pp. 3469-3471, 2001.
Ryo Akiyama et al., "A Novel Polymer-Supported Arene-Ruthenium Complex for Ring-Closing Olefin Metathesis", Angew. Chem., Int. Ed., 41, 2602-2604, 2002.
Shü Kobayashi et al., "Renaissance of immobilized catalysts. New types of polymer-supported catalysts, 'microencapsulated catalysts', which enable environmentally benign and powerful high-throughput organic synthesis", Chem. Commun., pp. 449-460, 2003.
Ryo Akiyama et al., "The Polymer Incarcerated Method for the Preparation of Highly Active Heterogeneous Palladium Catalysts", J. Am. Chem. Soc., 125, pp. 3412-3413, 2003.
Axel Jacobi von Wangelin et al., "Multicomponent Coupling Reactions for Organic Synthesis: Chemoselective Reactions with Amide—Aldehyde Mixtures", Chem. Eur. J., 9, pp. 4286-4294, 2003.
Ryo Akiyama et al., "Development of Amidocarbonylation Using Polymer Incarcerated Palladium Catalyst", CSJ: The Chemical Society of Japan Koen Yokoshu, vol. 84, No. 2, p. 1268, Mar. 11, 2004.

* cited by examiner

*Primary Examiner*—Daniel M Sullivan
*Assistant Examiner*—Yevegeny Valenrod
(74) *Attorney, Agent, or Firm*—Wenderoth, Lind & Ponack, L.L.P.

(57) ABSTRACT

A novel method of an amidocarbonylation reaction among an aldehyde compound, an amide compound, and carbon monoxide, which comprises using a palladium-supporting crosslinked-polymer composition containing palladium clusters having a major-axis length of 20 nm or shorter to conduct the amidocarbonylation reaction. Thus, an N-acyl-α-amino acid can be more efficiently and selectively synthesized in a dean reaction system. Also provided is a catalyst for use in the method.

4 Claims, No Drawings

METHOD OF AMIDOCARBONYLATION REACTION

FIELD OF INVENTION

The present invention relates to a novel method of an amidocarbonylation reaction that enables to recover and reuse a catalyst and can efficiently and according to a clean reaction system synthesize an amino acid compound that is important as one having various kinds of functions such as bioactivities or the like, and a catalyst therefor.

BACKGROUND ART

In a so-called Strecker reaction where from an aldehyde compound, ammonia and hydrogen cyanide α-amino nitrile is obtained, when α-amino nitrile that is a product is hydrolyzed, α-amino acid can be readily obtained. Accordingly, the Strecker reaction has long been used in a synthesis process of α-amino acid. However, there are problems in that high toxicity of a cyanide compound that is a raw material and an ammonium salt generated according to a hydrolysis reaction of α-amino nitrile have to be disposed of On the other hand, a so-called amidocarbonylation reaction where, from an aldehyde compound, an amide compound and carbon monoxide, N-acyl-α-amino acid is synthesized has many advantages over the Strecker reaction in that carbon monoxide lower in the toxicity than hydrogen cyanide is used, all raw materials are contained in a product (N-acyl-α-amino acid) to be an atom-economically highly efficient reaction, and furthermore according to a hydrolysis reaction not only an acyl group on nitrogen can be removed and converted into an α-amino acid but also the acyl group can be recovered as carboxylic acid and converted into a corresponding amide to enable to reuse as a raw material. In 1971, Wakamatsu et al found a method of carrying out an amidocarbonylation reaction having such excellent features under pressure of carbon monoxide/hydrogen with cobalt carbonyl that is a transition metal catalyst (non-patent literature 1, patent literature 1).

The Wakamatsu's method generally necessitates high-temperature and high-pressure conditions. On the other hand, in 1997, Beller et al reported an amidocarbonylation reaction that uses a palladium catalyst and a lithium bromide-sulfuric acid cocatalyst (non-patent literature 2, patent literature 2). This is an efficient reaction that does not necessitate hydrogen and can proceed under a lower catalyst amount, a lower carbon monoxide pressure and a lower temperature. Furthermore, Beller et al later reported of the catalyst activities of rhodium, iridium and ruthenium complexes under similar conditions (patent literature 3). Furthermore, more recently, the inventors of the present application found an amidocarbonylation reaction with a platinum catalyst (non-patent literature 3).

On the other hand, from a viewpoint of the organic synthetic chemistry, one of the most useful catalysts is a palladium catalyst. The polymer immobilization thereof has been studied for relatively long periods and many immobilized palladium catalysts have been developed. However, in many of so far developed polymer-immobilized catalysts, since a polymer and a metal portion that is an active center is connected with a ligand, though excellent in the stability, the activity of the catalyst itself is largely affected, and in many cases there is a problem in that the catalyst activity is lowered than that of a corresponding homogeneous system catalyst. Under such circumstances, the inventors of the application have developed a microencapsulated catalyst as a novel polymer-immobilized catalyst. The microencapsulated catalyst immobilizes a metal on a polymer by making use of a physical or an electrostatic interaction, consequently, the catalyst activity rivaling to or exceeding that of the homogeneous catalyst can be expected.

In actuality, the inventors have already developed a microencapsulated Lewis-acid catalyst, a microencapsulated osmium catalyst and a microencapsulated transition metal catalyst (palladium, ruthenium) and have reported that these catalysts worked effectively in various organic synthesis reactions (non-patent literature 4). However, since polystyrene hitherto used as a polymer carrier is dissolved with a reaction solvent in some cases, there is a problem in that the applications thereof are restricted. In this connection, the inventors studied to overcome the problem and developed a palladium catalyst having a novel configuration named as "a polymer Carcerand type (Polymer Incarcerated (PI)) catalyst (non-patent literature 5). In the catalyst, palladium is immobilized to a polymer (1) having an epoxy group and a hydroxyl group on a side chain as shown for instance with a formula below.

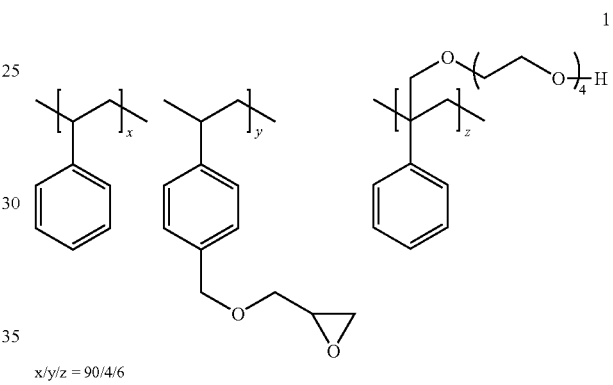

x/y/z = 90/4/6

More specifically, as shown in a formula below, firstly, palladium is carried or contained by a polymer according to a microencapsulation method, followed by heating under a non-solvent condition to crosslink polymers to render a palladium catalyst that is insoluble in an ordinary solvent. The catalyst effectively worked in a hydrogenation reaction of olefins and an allylic substitution reaction and generated in all cases a corresponding product at a high yield. Furthermore, in all cases, it is confirmed that palladium did not elute off and the catalyst could be recovered and reused.

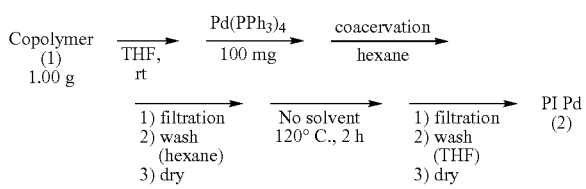

In this connection, the inventors have studied to make use of features of the novel palladium catalyst as mentioned above to realize the amidocarbonylation reaction method more efficiently and in a clean reaction system.

However, when, according to the report of Beller et al, with NMP (1-methyl-2-pyrolidinone) as a solvent, by use of the above-mentioned novel palladium catalyst: PI Pd (2), a reaction according to a formula below was tried, a yield of N-acyl- α-amino acid of only 9% or less was obtained. In the case of a dioxane solvent, the yield was only several percent.

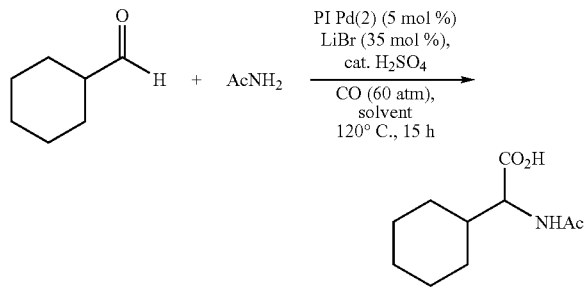

Non-patent literature 1: J. Chem. Soc., Chem. Commun., 1971, 1540

Non-patent literature 2: Angen. Chem. Int. Ed., 1997, 36, 1494

Non-patent literature 3: Chem. Lett., 2003, 160

Non-patent literature 4: (a) J. Am. Chem. Soc., 1998, 120, 2985. (b) J. Org. Chem., 1998, 63, 6094. (c) J. Am. Chem. Soc., 1999, 121, 11229. (d) Org. Lett., 2001, 3, 2649. (e) Angew. Chem., Int. Ed., 2001, 40, 3469. (f) Angew. Chem., Int. Ed., 2002, 41, 2602. (g) Chem. Commun., 2003, 449

Non-patent literature 5: J. Am. Chem. Soc., 2003, 125, 3412

Patent literature 1: DE-B 2115985 (1971)
Patent literature 2: DE-B 19627717 (1996)
Patent literature 3: DE 100 12251 A1 (1999)

SUMMARY OF INVENTION

The present invention, from the above-mentioned background, intends to provide a novel method of an amidocarbonylation reaction that, by taking advantages of features of the PI palladium catalyst that the inventors have developed and by further improving and developing the catalyst, can more efficiently and selectively carry out an amidocarbonylation reaction that enables one to synthesize N-acyl-α-amino acid in a clean reaction system.

The following features of the invention overcome the above problems.

[1] A method of amidocarbonylation reaction where an aldehyde compound represented by a formula below $$\underset{R^1}{\overset{O}{\|}}\!\!-\!\!H$$

($R^1$ in the formula expresses a hydrogen atom or a hydrocarbon group that may have a substitution group) is reacted with carbon monoxide and an amide compound represented by a formula below $$H_2N\!-\!\!\overset{O}{\underset{\|}{C}}\!\!-\!R^2$$

($R^2$ in the formula expresses a hydrocarbon group that may have a substitution group) to synthesize an amino acid compound represented by a formula below $$HO_2C\!-\!\!\underset{R^1}{\overset{}{C}}\!\!H\!-\!\!NH\!-\!\!\overset{O}{\underset{\|}{C}}\!\!-\!R^2$$

($R^1$ and $R^2$ in the formula are same as those shown above), characterized in that, in a reaction system, a palladium-supported crosslinked polymer composition containing palladium clusters having a major axis of 20 nm or less is present.

[2] The method of an amidocarbonylation reaction, characterized in that the palladium-supported crosslinked polymer composition is one that is obtained when a microcapsule containing palladium clusters is subjected to a crosslinking reaction.

[3] An amidocarbonylation reaction that uses a palladium-supported crosslinked polymer composition, characterized in that a microcapsule is made of a copolymer that includes a hydrophobic portion made of an aromatic group, an epoxy group and a hydrophilic portion that reacts with an epoxy group.

[4] The method of an amidocarbonylation reaction characterized in that the carried palladium has zero valence.

[5] A method of an amidocarbonylation reaction, characterized in that a polymer palladium catalyst is one that is obtained by immobilizing palladium in a copolymer of monomers containing styrene compounds represented by formulas (1), (2) and (3) below.

(1)

[styrene with $R^X$ at α-position and $R^Y$ at para-position]

(1a)

$-CH_2(OCH_2CH_2)_n\!-\!O\!-\!CH_2\!-\!\text{epoxide}$ (2)

[4-vinylphenyl-$(CH_2)_m\!-\!N(R^a)\!-\!C(O)\!-\!R^b$]

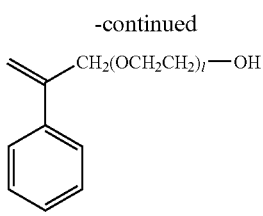

(3)

(In the formula, $R^x$ and $R^Y$ represent a hydrogen atom or a substitution group shown in a formula 1a, at least one of these showing a hydrogen atom, n showing an integer of 0 to 6, m showing an integer of 1 to 6, l showing an integer of 0 to 10, $R^a$ showing a hydrogen atom or a hydrocarbon group that may have a substitution group, $R^b$ showing a hydrocarbon group that may have a substitution group, and furthermore $R^a$ and $R^b$ may combine with each other to form a lactam ring.)

[6] A method of an amidocarbonylation reaction, characterized in that a copolymer is represented by a formula below.

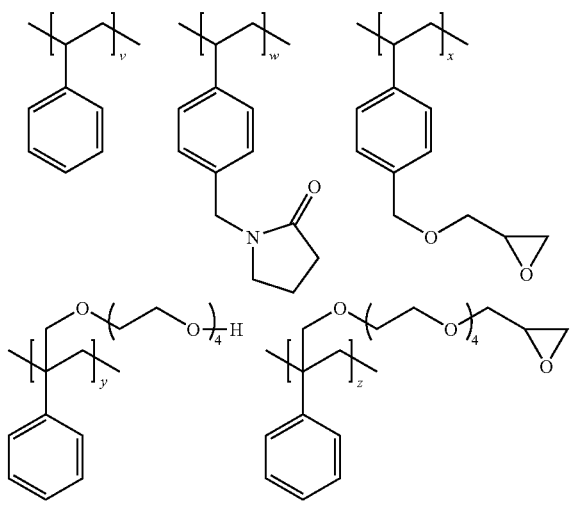

(In the formula, v/w/x/y/z is 0 to 90/3 to 80/0 to 20/3 to 20/0 to 20 and x and z are not zero.)

DETAILED DESCRIPTION OF THE INVENTION

The invention according to the application has features as mentioned above. In what follows, embodiments thereof will be described below.

Firstly, raw materials for an amidocarbonylation reaction that synthesizes N-acyl-α-amino acid are an aldehyde compound, an amide compound and carbon monoxide (CO). As to the aldehyde compound, a symbol $R^1$ in the formula is a hydrogen atom or a hydrocarbon group that may have a substitution group, and a symbol $R^2$ of the amide compound is a hydrocarbon group that may have a substitution group.

Here, the hydrocarbon group may be any one of various kinds such as an aliphatic hydrocarbon group, an alicyclic hydrocarbon group and an aromatic hydrocarbon group and may be saturated one or unsaturated one. Furthermore, the hydrocarbon group may form a ring through a different kind of atom (O, N, S or the like).

Furthermore, the substitution groups of the hydrocarbon groups, as far as these do not disturb the amidocarbonylation reaction, may be appropriately selected. Various kinds such as an alkoxy group, a nitro group, a heterocyclic group and so on may be considered.

A ratio of the aldehyde compound and the amide compound used as the raw materials, though not particularly restricted, is normally set preferably in the range of substantially 0.1 to 10 by mole ratio and more preferably in the range of 0.3 to 3. The carbon monoxide (CO), though not particularly restricted, is generally introduced in a reaction system under a pressure condition of substantially 10 to 80 atm.

In a reaction system of the amidocarbonylation reaction, a polymer palladium catalyst according to the invention of the application is contained. The polymer palladium catalyst is characterized as a palladium-supported crosslinked polymer composition containing palladium dusters having a major axis of 20 nm or less.

The palladium-supported crosslinked polymer composition, though not particularly restricted in the preparation thereof, is more preferably, for instance, one that is obtained by crosslinking microcapsules containing palladium clusters. In this case, various configurations of the microcapsules as well may be considered. However, preferably, a microcapsule made of a copolymer containing a hydrophobic portion made of an aromatic group, an epoxy group and a hydrophilic portion that reacts with an epoxy group can be cited.

As more preferable ones of the polymer palladium compositions, ones where palladium is immobilized to a copolymer of monomers that contain styrene and a styrene derivative represented as shown by formulas (1), (2) and (3) can be cited.

In the formula (1), $R^X$ and $R^Y$ in the formula are a hydrogen atom or a substitution group shown with a formula 1a, at least one of these showing at least one kind showing a hydrogen atom, n showing an integer of 0 to 6. Furthermore, in the formulas (2) and (3), m shows an integer of 1 to 6, l showing an integer of 0 to 10, $R^a$ showing a hydrogen atom or a hydrocarbon group that may have a substitution group, $R^b$ showing a hydrocarbon group that may have a substitution group, and furthermore $R^a$ and $R^b$ may combine with each other to form a lactam ring.

Furthermore, in the amide group of the formula (2), from viewpoints of the stability and the catalytic ability, $R^a$ and $R^b$ are more preferably one that bonds with a nitrogen atom to form a ring.

More specifically, when preferable examples are shown, the copolymers are, as shown above, ones that are represented with following formulas.

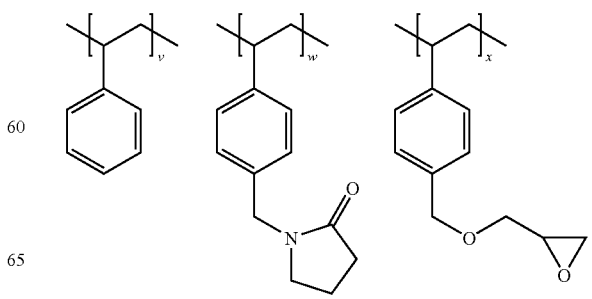

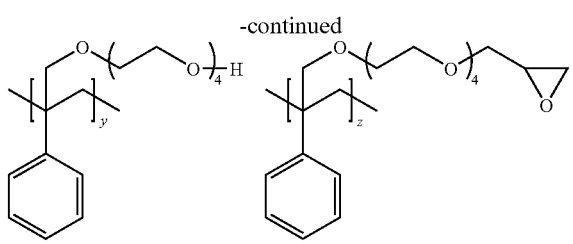

(In the formula, v/w/x/y/z is 0 to 90/3 to 80/0 to 20/3 to 20/0 to 20 and x and z are not zero.)

An average molecular weight of the polymer thereof is generally in the range of 5,000 to 150,000 by weight average molecular weight (Mw) and more preferably in the range of 15,000 to 100,000.

In order to suppress the immobilized palladium from eluting off and to make it insoluble in an ordinary solvent as well, in the polymer palladium catalyst according to the invention of the application, a heating process is effectively applied to facilitate the crosslinking.

Furthermore, unit coefficients w, x, y and z of the unit configurations such as shown above are as well determined from viewpoints of the stability of the palladium immobilization and the catalytic ability.

For instance, the polymer palladium catalyst according to the invention such as shown above can be prepared similarly to, for instance, a method that the inventors have proposed (non-patent literature 5). For instance, a process shown in a formula below can be cited.

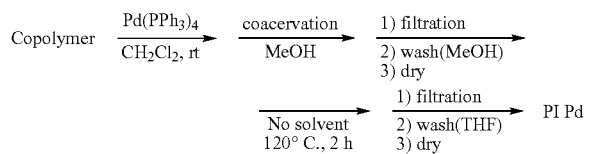

In general, in dissolution when for instance a process of microencapsulation is applied, polar good solvent: THF, dioxane, acetone, DMF, NMP and so on, nonpolar good solvent: toluene, dichloromethane, chloroform and so on, polar poor solvent: methanol, ethanol, butanol, amyl alcohol and so on, and nonpolar poor solvent: hexane, heptane, octane and so on are considered to be used.

At that time, as the conditions, the followings are considered That is, concentration of a polymer in a good solvent: 1 to 100 g/liter, concentration of a palladium catalyst in a good solvent: 1 to 100 mmol/liter and concentration of a poor solvent to a good solvent: 0.1 to 10 (v/v), preferably 0.5 to 5 (v/v).

Furthermore as the conditions of the thermal crosslinking temperature: 80 to 160° C., preferably 100 to 140° C. and reaction period: 30 min to 12 hr, preferably 1 to 4 hr can be considered.

In the amidocarbonylation reaction according to the invention of the application, the above-mentioned palladium-supported crosslinked polymer composition is used, as a molar ratio of palladium to reaction raw materials, normally in the range of 0.1 to 10% by mole, and more preferably in the range of 0.5 to 5% by mole. Together with the palladium-supported crosslinked polymer composition, in the reaction system, to the reaction raw materials, 10 to 15% by mole of a quaternary ammonium salt such as tetraalkyl ammonium bromide and 5 to 25% by mole of sulfuric acid are preferably added.

Furthermore, in the reaction, appropriate solvents can be used. Among these, dioxane is one of the preferable ones. A reaction temperature is generally in the range of 80 to 200° C.

The palladium-supported crosslinked polymer composition according to the invention of the application is effective not only in the amidocarbonylation reaction but also in various processes such as a hydrogenation reaction of olefins and so on.

In what follows, the invention will be detailed with reference to examples. It goes without saying that the invention is not restricted to examples below.

Examples

<1> A copolymer was prepared according to a reaction formula below

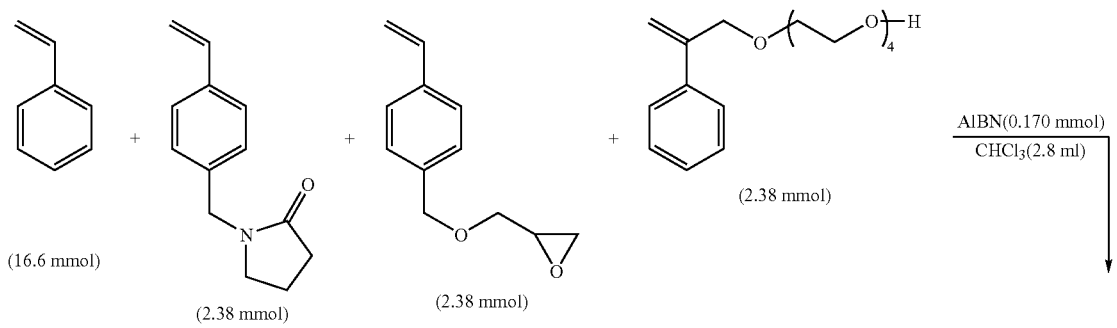

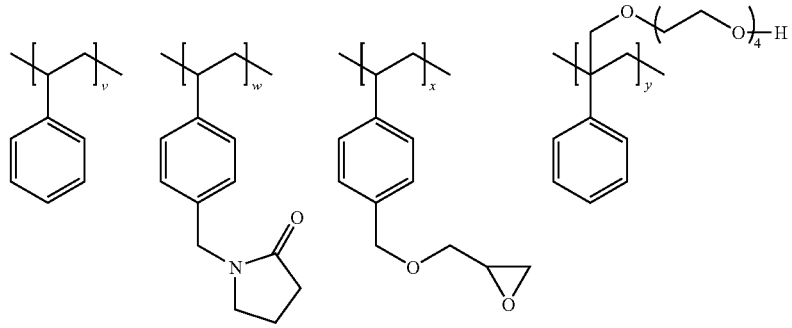

61% yield
($M_n$ = 32,911; $M_w$ = 80,978; $M_w/M_n$ = 2.461)

That is, styrene (1.75 g, 16.6 mmol), 1-(4'-vinylbenzyl)-2-pyrrolidinone (500 mg, 2.38 mmol), 4-vinylbenzyl glycidyl ether (452 mg, 2.38 mmol), tetraethylene glycol mono-2-phenyl-2-propenyl ether (738 mg, 2.38 mmol) and AIBN (28 mg, 0.17 mmol) were dissolved in chloroform (2.8 mL), followed by heating and stirring in an argon atmosphere for 48 hr under reflux. A reaction mixture was cooled to room temperature, followed by dropping into ice-cooled methanol (500 mL) to solidify a copolymer. After a supernatant liquid was removed according to the decantation, the copolymer was dissolved with a little amount of tetrahydrofuran, followed by once more dropping in ice-cooled methanol (500 mL). A precipitated copolymer was filtered and washed with methanol, followed by drying under reduced pressure under room temperature, and thereby 2.10 g of the copolymer (yield: 61%) was obtained.

A composition ratio (v/w/x/y) of the respective monomers, a number average molecular weight (Mn), a weight average molecular weight (Mw) and the degree of dispersion (Mw/Mn) of the obtained copolymer, respectively, were 71/13/10/6, 32,911, 80,978 and 2.461.

<2> In the next place, by use of the obtained copolymer, according to a process of a formula below, a palladium-supported crosslinked polymer composition was prepared.

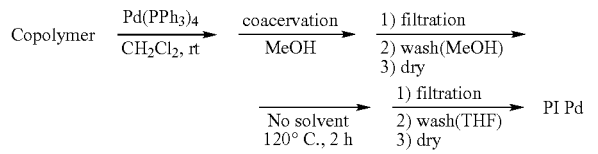

That is, the copolymer (1.0 g) and Pd (PPh3)4 (1.0 g) were dissolved in dichloromethane (20 ml) followed by stirring for 24 hr. Thereto, methanol (50 ml) was gradually added to agglomerate a palladium-containing copolymer. A supernatant liquid was removed according to the decantation, followed by washing several times with methanol, and then by drying under reduced pressure. Subsequently, under heating at 120° C. for 2 hr, the copolymers themselves were crosslinked. After washing with THF followed by drying, a palladium-supported crosslinked polymer was obtained (801 mg). A content of palladium was 0.82 mmol/g.

<3> With the palladium-supported crosslinked polymer composition prepared in the <2>, an amidocarbonylation reaction according to a formula below was carried out.

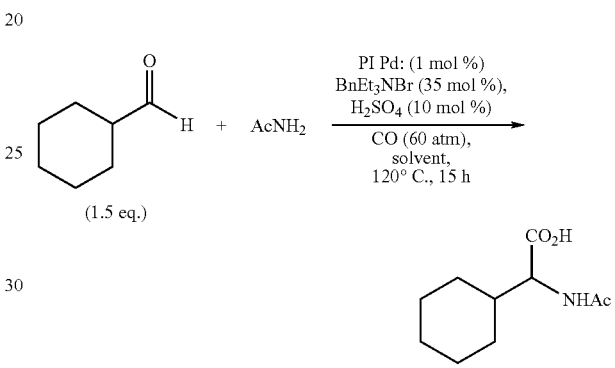

That is, the palladium-supported crosslinked polymer (12.2 mg, 0.01 mmol), acetamide (59.1 mg, 1.0 mmol), BnEt3NBr (95.3 mg, 0.35 mmol) and cyclohexane carboxaldehyde (168 mg, 1.5 mmol) were mixed in a 0.05M sulfuric acid-dioxane solution (2 mL, 0.10 mmol). A reaction vessel was put in an autoclave, followed by stirring under a carbon monoxide atmosphere of 60 atm at 120° C. for 15 hr. A reaction mixture was cooled to room temperature, followed by exhausting carbon monoxide and adding methanol (50 mL). After filtering to remove the catalyst, 2,6-xylenol that is an internal standard material was added to a filtrate, followed by analyzing by means of the HPLC to determine a yield (yield: 96%). The leakage of palladium (Pd) from the catalyst was not at all observed in the fluorescent X-ray analysis (XRF).

Furthermore, the reaction can isolate a targeted N-acyl-α-amino acid. That is, after the filtrate of the reaction was concentrated under reduced pressure, a residue was diluted with a saturated sodium hydrogen carbonate aqueous solution, followed by washing with chloroform and ethyl acetate. In the next place, after phosphoric acid was (I) added to an aqueous phase to adjust the pH to 2, followed by extracting with ethyl acetate, organic phases were gathered, further followed by drying with anhydrous sodium sulfate. After the filtration, the solution was concentrated under reduced pressure and thereby a targeted N-acyl-α-amino acid was obtained (isolation yield: 100%).

On the other band, a yield, when Et4NBr (35 mol %) was used as a quaternary ammonium salt, was 72% and that when Bu4NBr (35 mol %) was used was 98%.

When acetonitrile was used as the solvent, though a very slight amount of palladium eluted off, the yield was quantitative.

Similarly, various kinds of aldehyde compounds and amide compounds were reacted, and thereby N-acyl-α-amino acid could be synthesized with results below.

TABLE 1

Pl Pd[a] (1 mol %), BnEt$_3$NBr (35 mol %), H$_2$SO$_4$ (10 mol %), CO (60 atm), dioxane, 120° C., 15 h R$^1$CHO + H$_2$N-C(O)-R$^2$ (1.5 eq.) → HO$_2$C-CH(R$^1$)-NH-C(O)-R$^2$

| entry | R$^1$ | R$^2$ | yield (%)[b] |
|---|---|---|---|
| 1 | c-Hex | Me | quant (96)[c,d] |
| 2 | c-Hex | (CH$_2$)$_4$Me | 75[c] |
| 3 | c-Hex | Ph | 20[c] |
| 4 | c-Hex | NHMe | 20[c,e] |
| 5 | PhCH$_2$CH$_2$ | Me | 49[c,f] |
| 6 | i-Pr | Me | 67 |
| 7 | t-Bu | Me | 55 |
| 8 | Ph | Me | 78 |
| 9 | p-CF$_3$C$_6$H$_4$ | Me | 46[g] |
| 10 | p-MeOC$_6$H$_4$ | Me | 38 |
| 11 | α-Naph | Me | 58[g] |
| 12 | β-Naph | Me | 44[h] |

[a]Unless otherwise noted, the loading level of the palladium was 1.04 mmol/g.
[b]Isolated yields.
[c]Yield was determined by HPLC analysis.
[d]The loading level of the palladium was 0.820 mmol/g.
[e]The product was identified as 3.
[f]The reaction mixture was stirred at rt for 6 h before introducing CO.
[g]The loading level of the palladium was 0.629 mmol/g.
[h]The reaction was performed for 24 h.

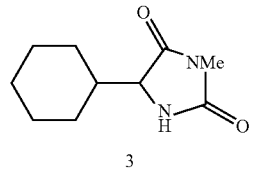

3

INDUSTRIAL APPLICABILITY

As mentioned above, according to the first feature of the invention, a synthesis of N-acyl-α-amino acid by an amidocarbonylation reaction that has many advantages over the above-mentioned Strecker reaction can be realized more efficiently and more selectively by use of a novel polymer-immobilized palladium catalyst in a clean reaction system while enabling one to recover and reuse the catalyst.

According to the second, third and fourth features of the invention, excellent advantages as mentioned above can be realized.

Furthermore, according to the fifth through eighth features of the invention, a palladium catalyst that can realize an amidocarbonylation reaction that exhibits excellent effects as mentioned above can be provided.

The invention claimed is:

1. In an amidocarbonylation reaction which comprises reacting an aldehyde compound represented by the formula

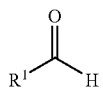

where R$^1$ is a hydrogen atom or a hydrocarbon group that may be substituted, with carbon monoxide and an amide compound represented by the formula

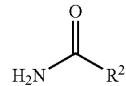

where R$^2$ is a hydrocarbon group that may be substituted, to produce an amino acid compound represented by the formula

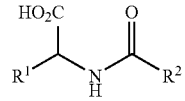

where R$^1$ and R$^2$ are the same as above, the improvement wherein the reaction is conducted in the presence of a palladium-supported crosslinked polymer composition containing a palladium cluster having a major axis of 20 nm or less; wherein the said palladium-supported crosslinked polymer composition is one obtained by immobilizing palladium to a copolymer of monomers containing styrene compounds represented by formulas (1), (2) and (3) below

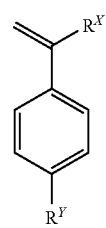

(1)

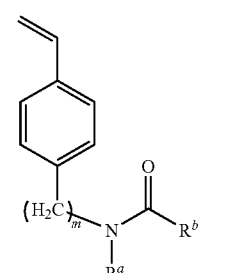

(2)

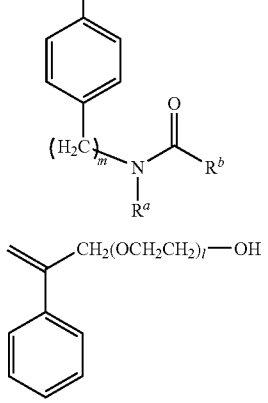

(3)

Where R$^X$ and R$^Y$ are hydrogen atom or a substitution group of formula (1a), at least one of R$^X$ and R$^Y$ being a hydrogen atom,

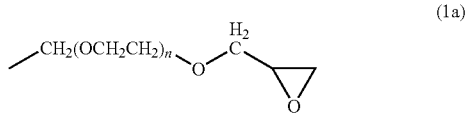

(1a)

n is an integer of 0 to 6, m is an integer of 1 to 6, l is an integer of 0 to 10, $R^a$ is a hydrogen atom or a hydrocarbon group that may be substituted, $R^b$ is a hydrocarbon group that may be substituted, and $R^a$ and $R^b$ may combine with each other to form a lactam ring.

2. The amidocarbonylation reaction according to claim 1, wherein the palladium has zero valence.

3. The amidocarbonylation reaction according to claim 1, wherein the copolymer is represented by the formula below

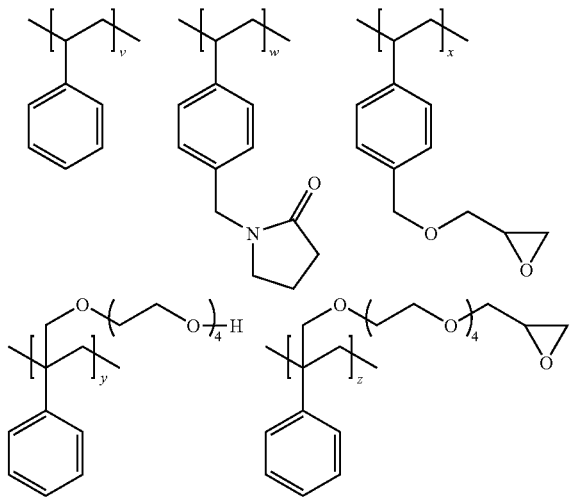

where v is 0-90, w is 3-80, x is 0-20, y is 3-20 and z is 0-20, with the proviso that x and z are not both zero.

4. The amidocarbonylation reaction according to claim 2, wherein the copolymer is represented by the formula below

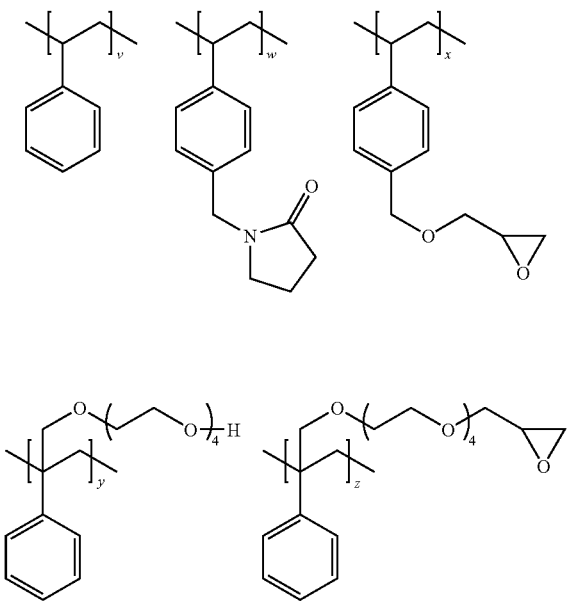

where v is 0-90, w is 3-80, x is 0-20, y is 3-20 and z is 0-20, with the proviso that z are not both zero.

* * * * *